US010166368B2

(12) United States Patent
Law

(10) Patent No.: US 10,166,368 B2
(45) Date of Patent: Jan. 1, 2019

(54) AUTONOMOUSLY CONTROLLABLE PULL WIRE INJECTION CATHETER, ROBOTIC SYSTEM COMPRISING SAID CATHETER AND METHOD FOR OPERATING THE SAME

(71) Applicant: Peter Law, Richmond Hill (CA)

(72) Inventor: Peter Law, Richmond Hill (CA)

( * ) Notice: Subject to any disclaimer, the term of this patent is extended or adjusted under 35 U.S.C. 154(b) by 0 days.

(21) Appl. No.: 15/711,308

(22) Filed: Sep. 21, 2017

(65) Prior Publication Data

US 2018/0078739 A1   Mar. 22, 2018

(30) Foreign Application Priority Data

Sep. 21, 2016 (WO) .................. PCT/IB2016/055617

(51) Int. Cl.
*A61M 25/01*   (2006.01)
*A61M 25/00*   (2006.01)
(Continued)

(52) U.S. Cl.
CPC ......... *A61M 25/0147* (2013.01); *A61B 5/055* (2013.01); *A61B 6/485* (2013.01); *A61B 8/12* (2013.01); *A61B 34/30* (2016.02); *A61B 34/32* (2016.02); *A61B 34/71* (2016.02); *A61M 25/005* (2013.01); *A61M 25/0084* (2013.01); *A61M 25/0662* (2013.01); *A61B 2018/00351* (2013.01); *A61B 2018/00642* (2013.01); *A61B 2018/00875* (2013.01); *A61B 2034/2051* (2016.02); *A61B 2034/301* (2016.02); *A61B 2090/064* (2016.02); *A61B 2090/065* (2016.02); *A61B 2090/374* (2016.02);
(Continued)

(58) Field of Classification Search
None
See application file for complete search history.

(56) References Cited

U.S. PATENT DOCUMENTS 5,130,141 A   7/1992   Law et al.
5,368,564 A   11/1994  Savage
(Continued)

FOREIGN PATENT DOCUMENTS

EP   1078644 A1    2/2001
EP   1 776 057 A1  4/2007
(Continued)

OTHER PUBLICATIONS

European Patent Office; Communication dated Feb. 15, 2018 in counterpart application No. 17192276.8.
(Continued)

*Primary Examiner* — Brian T Gedeon
(74) *Attorney, Agent, or Firm* — Sughrue Mion, PLLC

(57) ABSTRACT

An autonomously controllable pull wire injection 5 catheter 1 and a method for operating the same are provided. The catheter 1 includes an outer catheter guide 2, 33 having an outer catheter guide casing 39 and an inner operating catheter 3, 31 having an inner operating catheter casing 16, wherein the inner operating catheter 3, 31 includes a catheter handle 30, a catheter tip 10, at least one needle 5 that is connected to at least one source of medicinal solution via at least one needle 10 channel 4, 26, at least one contact force sensor 9a-f, 25, at least one electrode 7, 24, at least four actuator driven pull wires 12-15, 20-23 for moving the tip 10 of the inner operating catheter 3, 31.

15 Claims, 4 Drawing Sheets

(51) Int. Cl.

| | |
|---|---|
| *A61B 5/055* | (2006.01) |
| *A61B 6/00* | (2006.01) |
| *A61B 8/12* | (2006.01) |
| *A61M 25/06* | (2006.01) |
| *A61B 34/00* | (2016.01) |
| *A61B 34/32* | (2016.01) |
| *A61B 18/00* | (2006.01) |
| *A61B 90/00* | (2016.01) |
| *A61B 34/30* | (2016.01) |
| *A61B 34/20* | (2016.01) |

(52) U.S. Cl.
CPC ... *A61B 2090/376* (2016.02); *A61B 2090/378* (2016.02); *A61M 25/0041* (2013.01); *A61M 2025/0089* (2013.01); *A61M 2025/015* (2013.01); *A61M 2025/0166* (2013.01); *A61M 2205/332* (2013.01); *A61M 2205/3306* (2013.01); *A61M 2205/3317* (2013.01); *A61M 2205/50* (2013.01); *A61M 2205/70* (2013.01)

(56) References Cited

U.S. PATENT DOCUMENTS

| | | | |
|---|---|---|---|
| 5,567,612 | A | 10/1996 | Vacanti et al. |
| 6,015,671 | A | 1/2000 | Field |
| 6,051,648 | A | 4/2000 | Rhee et al. |
| 9,242,069 | B2 | 1/2016 | Alt et al. |
| 9,358,014 | B2 | 1/2016 | Cragg et al. |
| 2010/0204646 | A1 | 8/2010 | Plicchi et al. |
| 2015/0025381 | A1 | 1/2015 | Waters et al. |

FOREIGN PATENT DOCUMENTS

| | | |
|---|---|---|
| EP | 2 837 683 A1 | 2/2015 |
| WO | 02/28470 A1 | 4/2002 |
| WO | 2008/095032 A2 | 8/2008 |
| WO | 2009/092059 A2 | 7/2009 |

OTHER PUBLICATIONS

Prats-Boluda, G., et al., "Design and Development of an active Laplacian Sensor for non-invasive recordings of the intestinal bioelectrical signal", Biomedical Circuits and Systems Conference, Nov. 20, 2008, pp. 77-80 (4 pages), XP031398807.

Juan F. Granada, et al., "First-in-Human Evaluation of a Novel Robotic-Assisted Coronary Angioplasty System", JACC: Cardiovascular Interventions, Apr. 2011, pp. 460-465, vol. 4., No. 4.

Peter Law, et al., "Myoblast transfer as a platform technology of gene therapy", Gene Therapy and Molecular Biology, Mar. 1998, pp. 345-363, vol. 1.

Dariush Mozaffarian, et al., "Heart Disease and Stroke Statistics—2016 Update", AHA Statistical Update, Jan. 2016, 324 pages.

Peter K. Law, et al., "World's First Myoblast Treatment of Human Cancer Found Safe and Efficacious", Open Journal of Regenerative Medicine, Mar. 31, 2017, pp. 1-16, vol. 6.

International Search Report for PCT/IB2016/055617 dated Jun. 22, 2017 [PCT/ISA/210].

Written Opinion for PCT/IB2016/055617 dated Jun. 22, 2017 [PCT/ISA/237].

AUTONOMOUSLY CONTROLLABLE PULL WIRE INJECTION CATHETER, ROBOTIC SYSTEM COMPRISING SAID CATHETER AND METHOD FOR OPERATING THE SAME

This application claims priority from PCT Application No. PCT/IB2016/055617 filed Sep. 21, 2016, the contents of all of which are incorporated herein by reference in their entirety.

The present invention relates to an autonomously controllable pull wire injection catheter comprising an outer catheter guide having an outer catheter guide casing and an inner operating catheter having an inner operating catheter casing, wherein the inner operating catheter comprises a catheter handle, a catheter tip, at least one needle that is connected to at least one source of medicinal solution via at least one needle channel, at least one contact force sensor, at least one electrode, at least four actuator driven pull wires for moving the tip of the inner operating catheter, wherein the inner diameter of the outer catheter guide casing is larger than the outer diameter of the inner operating catheter casing. The invention also relates to a robotic system comprising said catheter and a method for operating the same.

In 2012, the World Health Organization (WHO) estimated that cardiovascular disease (CVD) was the leading cause of death affecting 17.5 million people across the globe. Of these fatalities, 7.4 million were the result of ischemic heart disease. Myocardial infarction (MI), a potential consequence of myocardial ischemia, signifies cardiac muscle damage where the cells undergo necrosis and apoptosis [Miller J M, Dixon M A, Bhakta D, Rahul J, Das M K (2015) Magnetic and robotic catheter navigation. In: Steinberg J S, Jais P, Calkins H (eds) Practical Guide to Catheter Ablation of Atrial Fibrillation. John Wiley & Sons Ltd., UK, pp 75-83], eventually forming a permanent scar on the ventricular wall. With scar tissue having low electrical conductivity and thus being unable to contract, the heart's functionality and ability to pump efficiently is deteriorated, likely leading to congestive heart failure.

The ideal treatment for MI is still a developing science. Given the mortal significance of MI and the challenges faced with current treatment plans, extensive research has been invested into novel treatment methods. In recent years, cell transfer therapy has undergone significant progress and has been studied extensively in clinical trials. These types of transferred cells consist of embryonic stem cells, induced pluripotent stem cells, human umbilical cord cells, fetal cardiomyocytes, skeletal myoblasts, resident cardiac stem cells, bone-marrow-derived stem cells, and mesenchymal stem cells. The underlying principle of committed myogenic or undifferentiated stem cell transfer is in the regeneration of myocardial tissue when the cell solutions are delivered to an infarct area. The method of transfer for these reparatory cells to the damaged myocardial site may be accomplished by means of intravenous (peripheral) infusion, subcutaneous cytokine injection, coronary sinus infusion, intracoronary infusion, and direct intramyocardial injection using an intracardiac catheter (transendocardial) or through open chest surgery (transepicardial) [see e.g. Granada J F, Delgado J A, Uribe M P, Fernandez A, Blanco G, Leon M B, Weisz G (2011) First-in-human evaluation of a novel robotic-assisted coronary angioplasty system. JACC Cardiovasc Interv 4:460-465. doi: 10.1016/j.jcin.2010.12.007; Law P K, Goodwin T G, Fang Q, Vastagh G, Jordan T, Jackson T et al (1998) Myoblast Transfer as a Platform Technology of Gene Therapy. Gene Ther Mol Biol 1:345-363].].

The use of catheters in interventional cardiac diagnostics has become preferred for patients with over 2.7 million catheter-based procedures performed per year in the United States [D. Mozaffarian et al. (2016, January). AHA Statistical Update. Heart Disease and Stroke Statistics—2016 Updated. Circulation. [Online]. 133(4), pp. e38-360. Available: http://circ.ahajournals.org/content/133/4/e38]. Manually controlled catheters function by means of a physician manipulating the catheter handle (i.e. proximal end) where distal torque, deflection, and linear movement may be applied to the catheter, depending on the catheter's design. An imaging system such as x-ray fluoroscopy is typically used to provide visual feedback for the physician. Preshaped catheters, guidewires and catheter sheaths are also used to assist in the insertion and placement of the catheter. A developing technology involves the use of remotely controlled magnetic and active catheters where physicians may perform catheterization procedures from a distance or at a separate workstation.

Catheters and catheter systems are already known.

WO 2009/092059 discloses a system for remote manipulation and positioning within the body of a patient of an elongated medical device having a proximal portion, the system comprising:

a robotic device comprising: a handle controller configured to receive the proximal portion of the elongated medical device; a sled member coupled to the handle controller; and a sled base configured to advance the sled member along a guide towards the body of the patient, said sled base being coupled to a sterile barrier effective to maintain sterility inside said sled base by means of a resealable delivery channel effective to receive and guide the elongated medical device; and a remote controller.

U.S. Pat. No. 9,242,069 B2 discloses a method of delivering stem cells to a failing organ in a patient's body, comprising:

selecting a catheter dimensioned for a selected failing organ, wherein the catheter comprises a proximal portion and a distal portion and has a continuous central lumen extending from the proximal portion into the distal portion, wherein the diameter of the lumen in the distal portion is smaller than the diameter of the lumen in the proximal portion, and wherein an outer diameter of the distal portion is dimensioned to fit into a duct or vessel of the failing organ to a target site of damaged tissue of the failing organ;

inserting the selected catheter into the duct or vessel of the failing organ and advancing the catheter to a location proximate the target site;

occluding the duct or vessel upstream of the target site by inflating a distally affixed balloon on the catheter;

injecting under a selected desired pressure a fluid containing stem cells through the catheter for ejection under pressure from the central lumen at the distal tip of the catheter proximate the target site, while measuring the injection pressure; and adjusting the injection pressure of the fluid containing the stem cells flowing through the catheter to the selected desired pressure by a closed loop system coupled to the catheter.

US 2015/0025381 A1 discloses a method for providing image-guided transendocardial injection of a therapeutic agent into a left ventricular wall of a heart, comprising:

providing an endoventricular injection catheter having integrated echocardiographic capability, the endoventricular injection catheter having an elongated body with a first housing, a second housing and a distal section positioned distal to the second housing in a longitudinal direction, the distal section having a distal end and an imaging core and an injection system carried on the elongated body with the imaging core;

positioning the endoventricular injection catheter into the left ventricle of the heart, thereby inserting the imaging core into a heart;

transmitting ultrasonic energy via the imaging core;

visualizing the left ventricular wall of the heart using the imaging core;

identifying infarct regions of the left ventricle; and injecting a therapeutic agent into the visualized infarcted regions of the left ventricle using the injection system.

WO 02/28470 A1 discloses a method of delivering myogenic cells into a degenerative or weak muscle in a host, comprising the steps of placing a catheter within the host, the catheter comprising a sensor on its tip to detect contact with degenerative or weak muscle tissue; and expelling the myogenic cells through a needle in the tip of the catheter into and/or around the degenerative or weak muscle upon sensing contact with degenerative or weak muscle tissue.

U.S. Pat. No. 9,358,014 B2 discloses a system comprising: an inner catheter defining an inner lumen; an outer catheter defining an outer catheter lumen and a plurality of side ports, wherein the outer catheter surrounds the inner catheter, a distal end of the outer catheter forming a fluid tight seal with an exterior surface of the inner catheter when a distal end of the inner catheter extends past the distal end of the outer catheter, wherein the inner catheter is slideable with respect to the outer catheter to adjust a distance between the distal end of the inner catheter and the side ports; a liquid embolic composition source fluidically connected to the inner catheter lumen; and a disruption fluid source fluidically connected to the outer catheter lumen, the disruption fluid comprising saline, a contrast medium, or a mixture of saline and the contrast medium.

In view of this situation, an object underlying the present invention is to provide a practical, yet effective autonomously controllable pull wire injection catheter, a robotic system that can autonomously perform injection procedures and a process for operating the same.

In accordance with the present invention, this object is achieved by an autonomously controllable pull wire injection catheter; a robotic system comprising said autonomously controllable pull wire injection catheter and a process for operating the robotic system with the features of the independent claims. Preferred embodiments of the invention are detailed in the respective dependent claims. Preferred embodiments of the pull wire injection catheter and the robotic system correspond to preferred embodiments of the process, even if they are not referred to herein in detail.

The invention is thus directed to an autonomously controllable pull wire injection catheter comprising an outer catheter guide having an outer catheter guide casing and an inner operating catheter having an inner operating catheter casing, wherein the inner operating catheter comprises a catheter handle, a catheter tip, at least one needle that is connected to at least one source of medicinal solution via at least one needle channel, at least one contact force sensor, at least one electrode, at least four actuator driven pull wires for moving the tip of the inner operating catheter, wherein the inner diameter of the outer catheter guide casing is larger than the outer diameter of the inner operating catheter casing, wherein the inner operating catheter is adapted to be controlled by a microcontroller, wherein the at least one electrode and the at least one contact force sensor are adapted for data exchange with the microcontroller, and wherein the at least four actuator driven pull wires are attached inside the inner operating catheter perpendicular to each other at a pre-defined distance from the tip in the distal region.

The term "autonomously" in the meaning of the invention is defined as without human participation. An autonomously controlled catheter is thus for example a catheter that can be used with a robotic system, wherein the robotic system carries out the movement otherwise performed by a physician and wherein a microcontroller steers and controls the respective medical procedure for example based on an implemented software algorithm and/or sensor signals. According to the invention the level of autonomy is not restricted. If a medical procedure requires for example a sequence of 4 steps, just one or two steps may be carried out autonomously or even the whole sequence. The remaining steps of the medical procedure may then be carried out by a physician either manually or remotely. It may also be possible to change between autonomous, remote and manual control at any time during a medical procedure to allow the physician to interact for example in case of an emergency.

According to the invention the autonomously controllable pull wire injection catheter comprises an outer catheter guide having an outer catheter guide casing and an inner operating catheter having an inner operating catheter casing. Casing in the meaning of the invention is a tube, sleeve or hose shaped cover having a defined wall thickness and preferably, but not necessarily a circular cross section. The cross section can be constant along the length of the casing or may become smaller or larger or may even vary in one or more sections of the casing. Preferably, the casing is made of flexible material allowing it to be deformed when necessary.

Generally, the purpose of the outer catheter guide is to provide stability and passage for the inner operating catheter while it is in operation. According to the present invention the inner diameter of the outer catheter guide casing is thus larger than the outer diameter of the inner operating catheter casing. In this way, the inner operating catheter may be passed through the outer catheter guide to a desired destination inside a patient's body, for example the left ventricle of a beating heart.

Design and features of the outer catheter guide are not restricted according to the invention. The outer catheter guide may be steerable. Advantageously, the outer catheter guide can then be manually rotated or deflected for example by at least one pull wire. The outer catheter guide may also be used in combination with a guide wire to reach its destination in a patient's body. Moreover, the outer catheter guide may also be pre-shaped. A pre-shaped outer catheter guide may stabilize itself inside a patient's body by creating contact points with for example an aortic wall. The casing of the outer catheter guide may also be lined with a shape memory alloy such as nickel titanium allowing for more flexibility and easy deformation.

According to the invention the inner operating catheter comprises a catheter handle. In general, the catheter handle is disposed in the so-called proximal region of the inner operating catheter. The proximal region is usually the region of the catheter that is not inserted into a patient's body.

According to the invention the inner operating catheter is adapted to be controlled by a microcontroller. For example, if the inner operating catheter is connected to a robotic system, the microcontroller may then steer and control the catheter operation via the robotic system that performs the respective movements instead of a physician.

Preferably, the inner operating catheter handle thus comprises mechanical and electrical connectors, such as actuators or female connectors that allow establishing a connection to a robotic system.

For example, two actuators may be foreseen to control an insertion of the at least one needle of the inner operating catheter into tissue for example and the injection of a medicinal solution. If more needles are foreseen, the above described arrangement may be multiplied.

According to the invention the inner operating catheter comprises a tip. The tip is generally located at the end of the inner operating catheter that is inserted into a patient's body. This region is usually called the distal region of the catheter. The realization of the tip is not restricted according to the invention. The tip can be a part of the inner operating catheter casing for example. But, the tip may also be formed as a separate part that can be attached to the end of the catheter casing. However, in any case the tip of the inner operating catheter is preferably tapered. Advantageously, the tip further comprises at least one protective casing for the retraction and storage of the at least one needle of the inner operating catheter.

The inner operating catheter handle, the inner operating catheter casing and the inner operating catheter tip are usually connected as such that they form an entity. The handle represents the end in the proximal region and the tip represents the end in the distal region. The casing forms the part in between, wherein the length of the casing is not restricted and will be chosen according to the use of the inner operating catheter.

The material for forming the inner operating catheter casing is not restricted according to the invention. Preferably, a flexible material is used at least for the tip to allow moving the tip inside a patient's body if necessary.

In a preferred embodiment the inner operating catheter casing consists of three layers with an outer layer of thermoplastic polyurethane (TPU), a braided or coiled stainless steel middle layer, and an inner layer of polytetrafluoroethylene (PTFE). The outer diameter of the inner operating catheter casing is also not restricted according to the invention. However, preferably a casing having an outer diameter of from 2-4 mm is used, for example 2.7 mm.

Usually, a pull wire is used to move the tip by pulling or disengaging the pull wire from the proximal region of the inner operating catheter. A pull wire thus generally extends from the proximal region to a defined position in the distal region of an inner operating catheter.

According to the invention the inner operating catheter comprises at least four actuator driven pull wires. The type of actuators used to drive the pull wires is not restricted according to the invention as long as the respective pulling and disengaging of the pull wire can be performed via a connection to a robotic system. In a preferred embodiment, however, bipolar four wire stepper motors are used as actuators, for example NEMA 17 42×42 mm. Preferably, the actuators are disposed in the inner operating catheter handle.

To pass the pull wires along the length of the catheter from the proximal region to the distal region, the pull wires may be embedded in the wall of the inner operating catheter casing or may be lead through the inner hollow part of the inner operating catheter casing. In the latter case, the wires are preferably enclosed by one or more tubes.

According to the invention the at least four actuator driven pull wires are attached inside the inner operating catheter perpendicular to each other at a pre-defined distance from the tip in the distal region. In this way, a 360° movement of the catheter tip may be achieved by pulling and/or disengaging the respective pull wires.

The pre-defined distance from the tip is not restricted according to the invention and usually depends on the size of the tip and its deformability. However, preferably the distance is the same for all of the at least four pull wires.

It is also possible to add more pull wires at different longitudinal points along the catheter casing. In a preferred embodiment the inner operating catheter thus comprises eight actuator driven pull wires. In this way, the pull wires allow the catheter to bend in an S-like shape as opposed to just one curve.

According to the invention the autonomously controllable pull wire injection catheter comprises at least one contact force sensor. In a preferred embodiment the at least one contact force sensor is a fiber optic sensor. A fiber optic sensor has a low expense, is nonconductive and electrically passive, does not rise in temperature while operating and is immune to electromagnetic interference.

Preferably, at least one single mode fiber having a diameter ≤250 μm is used to create the fiber optic sensor. The optical fiber measures the compression of an elastic material (i.e. silicone rubber) or the compression of a spring mechanism caused by the contact force exerted at the inner operating catheter tip. The method of measuring this displacement may be intrinsic or extrinsic where the measured light is respectively reflected inside or outside of the fiber.

More preferably, at least one equilaterally fiber bragg grating (FBG) optical fiber is used, for example three equilaterally fiber bragg grating (FBG) optical fibers.

Usually, the at least one contact force sensor detects the contact force created when the inner operating catheter tip and/or the at least one needle touches a surface inside a patient's body. The at least one contact force sensor is thus preferably arranged in the vicinity of or at the tip of the inner operating catheter depending on the type of contact force sensor used and its sensitivity.

According to the present invention the at least one contact force sensor is adapted for data exchange with the microcontroller. The way in which this data exchange is realized is not restricted according to the invention. The data exchange may be established by a wired or a wireless connection.

Generally, during a medical procedure applying an injection catheter, injection sites have to be determined. Sensor signals may be used to determine whether or not a tissue is damage or degenerated. In the case of myocardial infarcts in the endocardium for example measuring the electrical potential of the tissue may be utilized. Damaged and/or degenerated areas then usually show electrical silence, lower electrical activity or abnormal echocardiograms.

According to the present invention the inner operating catheter comprises at least one electrode. The type of electrode used and its arrangement within the inner operating catheter is not restricted according to the invention and may be chosen depending on the medical procedure and/or the environment the autonomously controllable pull wire injection catheter is used in. For example, the at least one electrode may be unipolar, bipolar or tripolar. Preferably, however, the at least one electrode is disposed in the vicinity of or at the tip of the inner operating catheter. The number of electrodes used is not restricted. The inner operating catheter may comprise two or more, for example three electrodes. The electrodes may be of the same type or different.

In a preferred embodiment, the at least one electrode is adapted to operate in Laplacian mode.

The Laplacian method uses equidistant electrodes on a 2D plane surrounding a target electrode to generate a local signal independent of the direction of the wave front. The calculation for the Laplacian signal can be obtained by the difference between the signal received by the central electrode and the mean or weighted sum of the surrounding electrodes.

According to the present invention the inner operating catheter also comprises at least one needle that is connected to at least one source of medicinal solution via at least one needle channel. A needle channel is thus a channel to transport medicinal solution from the at least one source to the needle. The at least one source may be a syringe for example. Usually, the at least one needle channel is disposed inside the hollow part of the inner operating catheter casing, this arrangement is, however, not limiting. Other arrangements may be possible.

The at least one needle is usually disposed in the distal region of the inner operating catheter, preferably at the tip of the inner operating catheter. The tip is preferably tapered to allow insertion of the needle into or penetration of a body cavity of a patient such as a femoral artery or coronary artery. More preferably, the tip also comprises a protective casing for the retraction of the at least one needle after injection and storage of the at least one needle of during insertion and removal of the catheter with respect to the body of a patient.

In a preferred embodiment the at least one needle can be triggered to protrude from the catheter tip by a defined distance.

The at least one needle usually exits from the surface of the tip. In an embodiment the needle may exit from a corner of the tip. In another embodiment the needle may exit from a side of the tip. The number of needles comprised in the inner operating catheter is not restricted according to the invention. The inner operating catheter may comprise two or more needles that may all exit from the surface the catheter tip. The needles may, however, also exit from different parts of the tip, for example from the end and from a corner and/or side of the tip.

The at least one needle may also be pre-shaped. A shape memory alloy, for example nickel titanium alloy, may be used for this purpose. A pre-shaped curved needle is advantageous as it allows injecting a medicinal solution diagonally. It was found that in case of a cell solution injecting diagonally while the needle is retracting yields a better cell distribution and a higher cell fusion rate.

Preferably, the needle size is of from 0.9 mm (20 gauge) to 0.3 mm (30 gauge), more preferably of from 0.45 mm (26 gauge) to 0.55 mm (24 gauge). In this way, a balance between fitting within the inner operating catheter casing and achieving maximal cell retention, in case the medicinal solution is a cell solution, can be obtained.

In a preferred embodiment the needle is inserted into the left ventricle of a beating heart of a patient. In this case, the needle may protrude from the surface of the inner operating catheter tip of from 3 to 12 mm, preferably of from 5 to 10 mm and more preferably, for regular non-degenerative adult hearts, of from 6 to 8 mm as measured from the surface of the tip.

During an injection the opening for the at least one needle at the catheter tip may be a cause for thrombosis and may allow blood to enter the inside of the inner operating catheter. In a preferred embodiment the inner operating catheter thus comprises an anticoagulant channel. The arrangement of the anticoagulant channel in the inner operating catheter is not restricted. Preferably, the anticoagulant channel merges, however, to the needle channel in the distal region. An anticoagulant may then be pumped through the channel where it emerges inside the needle channel. This can prevent blood from entering the inner operating catheter and prevent coagulation of blood at the opening. Preferably, heparin may be used as anticoagulant.

In a preferred embodiment the autonomously controllable pull wire cell injection catheter further comprises an electromagnetic position sensor. An electromagnetic position sensor can be used to provide feedback on the position and orientation of the catheter once placed in a desired surrounding, e.g. into the body of a patient. Using anatomic landmarks, the position can be related to the patient's body using a base image taken by means of an X-ray, CT, MRI, PET or ultrasound unit prior to an operation. To provide real-time images of the patient's body during operation, however, fluoroscopy may be used in combination with the electromagnetic position sensor.

In a preferred embodiment, the autonomously controllable pull wire injection catheter may be used in combination with a 3D or 4D ultrasound imaging unit. In this way, a feedback image can be provided where the catheter position is determined by an image analysis algorithm implemented in the microcontroller controlling the operation of the catheter.

In a more preferred embodiment, the 3D or 4D ultrasound imaging unit may be adapted to be controlled by a microcontroller. Preferably, the ultrasound imaging unit then comprises a transducer. More preferably, the ultrasound imaging unit then further comprises at least one contact force sensor. Advantageously, the at least one contact force sensor may be disposed at a contact point of the ultrasound imaging unit with a patient's body. If more contact points are foreseen, the ultrasound imaging unit may comprise more contact force sensors, respectively. In this way, it may be determined if there is too much or not enough contact with a patient's body. If required, the angle of contact may also be determined. During a medical procedure, autonomous movement of the transducer may thus be achieved, where a microcontroller may move the transducer back and forth between the appropriate locations on the patient's body. The images taken by the ultrasound imaging unit may then be relayed to an algorithm implemented in the microcontroller to determine where the autonomously controllable pull wire injection catheter is located in the patient's body.

In another preferred embodiment, the autonomously controllable pull wire injection catheter may be used in combination with a magnetic resonance imaging (MRI) unit. Preferably, the MRI unit is then adapted to be controlled by a microcontroller.

According to the invention the inner operating catheter comprises at least one needle that that is connected to at least one source of medicinal solution. In a preferred embodiment, the at least one medicinal solution is a cell solution.

A wide range of cells may be advantageously used with the inner operating catheter of the autonomously controllable pull wire injection catheter according to the invention, as described for example in U.S. Pat. Nos. 5,130,141 and 6,015,671. In each case, the cells are provided in aqueous suspension with one or more optional polymers for mechanical stabilization and/or to improve subsequent attachment to the site of the delivery. Examples of suspension media and suitable optional polymers are provided in U.S. Pat. No. 5,567,612.

Specialized cell media may be used in conjunction with the catheter. In one embodiment a polymer is included to minimize leakage and/or movement of cells after injection into the myocardium. Polymers preferred for this use include for example those described in U.S. Pat. No. 6,051,648.

In a particularly preferred embodiment the at least one medicinal solution is a myoblast solution having a concentration of $7.5\times10^8$ cells/mL to $1.5\times10^9$ cells/mL, for example $10\times10^8$ cells/mL.

Polymers and binding agents that adhere to muscle cells and myocardium tissue are thus particularly preferred for the aqueous suspension, and may be used in combination with polymers and other substances that bind and hold myogenic cells in place for a period of time before dissolution or release of the binding agents. The concentration and average sizes of polymers used for these purposes will be readily determined through routine experimentation and chosen to minimize viscosity of the injected cell suspension. In one embodiment freshly oxygenated red cells are included in the media to maintain aerobic respiration of myogenic cells that are loaded and remain within the catheter for a period of time prior to their injection.

The invention is also directed to a robotic system comprising an autonomously controllable pull wire injection catheter according to the invention, a robotic arm, a microcontroller, a holder and contraption for at least one source of medicinal solution, wherein the robotic arm is manoeuvrable at least in forward and backward direction, wherein the inner operating catheter of the autonomously controllable pull wire injection catheter is fixed onto the robotic arm as such that the catheter handle, the at least one needle, the at least one contact force sensor, the at least one electrode, and each of the at least four actuator driven pull wires are separately connected to the robotic arm, and wherein the robotic arm is adapted to be controlled by the microcontroller.

Generally, in order to assemble a robotic system fixing means are used. According to the invention the fixing means are not restricted and may be chosen depending on their use. Fixing means may be for example bolds, nuts, ball bearings, mechanical slides or other mechanical elements. The material the fixing means are made of is also not restricted and will be chosen according to the use.

According to the invention the robotic arm is manoeuvrable at least in forward and backward direction. The maneuverability of the robotic arm may be realized in any way that appears suitable. The robotic arm may for example be fixed onto a mechanical slide that can be moved by an actuator.

The robotic arm may for example also be manoeuvered by a robotic handle. The robotic handle may be designed as a container for the robotic arm allowing it to slide back and forth. Movement in other directions may also be possible, even omnidirectional movement. This may depend on the design of the robotic handle, which is not restricted.

According to the invention the robotic arm, however, is adapted to be controlled by the microcontroller. The way in which this control is established is not restricted. If a robotic handle is used the robotic arm may be controlled by the microcontroller at least in parts via controlling the robotic handle. The control may be furthermore established by wired or wireless connections, this is not restricted.

According to the invention the inner operating catheter of the autonomously controllable pull wire injection catheter is fixed onto the robotic arm as such that the catheter handle, the at least one needle, the at least one contact force sensor, the at least one electrode, and each of the at least four actuator driven pull wires are separately connected to the robotic arm.

Preferably, the handle of the inner operating catheter is fixed onto the robotic arm as such that it moves integrally with the robotic arm. Hence, when the robotic arm moves in forward direction, the handle of the inner operating catheter will move forward together with the robotic arm. As described above, the inner operating catheter handle, the catheter casing and the tip usually form an entity. Thus, if the catheter handle moves forward integrally with the robotic arm, the casing and the tip will do as well. In this way, the inner operating catheter may be moved through the robotic arm for example through the outer catheter guide and/or inside a patient's body according to an input from the microcontroller, which controls the robotic arm.

Generally, once the inner operating catheter has reached a desired destination, for example when the tip of the catheter is situated on the endocardium wall of a left ventricle of a beating heart, the inner operating catheter is locked in place. The robotic arm may thus further comprise at least one locking means.

According to the invention the catheter handle, the at least one needle, the at least one contact force sensor, the at least one electrode, and each of the at least four actuator driven pull wires are separately connected to the robotic arm. The robotic arm may thus comprise separate connectors accordingly. The type of connectors used is not restricted according to the invention. In the case of the at least one electrode and the at least one contact force sensor it is foreseen that a data exchange is possible with the microcontroller. The connection may in this case be a wired or wireless data connection.

In any way, it is particularly preferably that the separate connections are chosen as such that the at least one needle, the at least one contact force sensor, the at least one electrode and each of the at least four actuator driven pull wires maintain their relative position in the inner operating catheter when the inner operating catheter handle is moved by the robotic arm. In this way, any damage to a patient's body can be prevented during the insertion and removal of the inner operating catheter and the inner operating catheter can be operated in an optimal manner when it has reached its destination inside the patient's body.

According to the invention the robotic system comprises a microcontroller. The microcontroller is adapted to control the robotic arm. Via the robotic arm the microcontroller may steer and control the operation of the inner operating catheter during the performance of a medical procedure for example.

In a preferred embodiment the microcontroller is configured to control the robotic arm and hence the inner operating catheter based on a feedforward control.

Feedforward in the meaning of the invention refers to a software algorithm type of control that uses mathematical models, empirical data, imaging techniques and/or medical results to control the operation of the robotic arm and with it the inner operating catheter.

If the operating environment is the left ventricle of a heart for example, a 3D model of a left ventricle may be used to accomplish the feedforward control.

The microcontroller may additionally or alternatively also use a feedback control. Feedback in the meaning of the invention refers to a measurement based control. For example, the microcontroller may induce a sensor measurement and may then determine how to operate the robotic arm and with it the inner operating catheter based on the evaluated results. Feedback may be obtained from sensors and/or imaging techniques.

Sensor feedback such as electrical information feedback for example may be provided by the at least one electrode disposed at the tip of the inner operating catheter. The at least one electrode may be used to provide e.g. electrical conductivity (resistance), high impedance voltage measurements or low impedance current measurements to the microcontroller.

Feedforward and feedback control can be advantageously used in combination. For example, if an imaging unit is provided, the positional behavior of the inner operating catheter tip relative to the displacement of the actuators can be mapped onto an existing mathematical model of the operating environment by the microcontroller.

In an embodiment the robotic system further comprises an imaging unit selected from the group consisting of an ultrasound unit, a magnetic resonance unit or a fluoroscopy unit.

In a more preferred embodiment the imaging unit is a 3D or 4D ultrasound unit. Preferably, the 3D or 4D ultrasound unit is then adapted to be controlled by the microcontroller. For example, at least parts of the ultrasound unit may thus be attached to the robotic arm. More preferably, the ultrasound unit then comprises at least one transducer and at least one contact force sensor. In another preferred embodiment, the imaging unit is a magnetic resonance (MRI) unit. Preferably, the magnetic resonance unit is then adapted to be controlled by the microcontroller. For example, at least parts of the MRI unit may thus be attached to the robotic arm.

In another embodiment the robotic system may further comprise a stabilizing arm to hold the outer catheter guide of the autonomously controllable pull wire injection catheter in place once it has reached its destination in a patient. Therefore, the outer catheter guide handle may be locked by a locking means for example.

The material out of which at least parts of the robotic system are made is not restricted according to the invention. Any material and/or material combinations and/or mixtures of materials may be used. In a preferred embodiment, however, the robotic arm is made up of at least 70% of polylactid acid.

According to the invention the robotic system comprises a holder and contraption for at least one source of medicinal solution. The type of source is not restricted according to the invention it may be a reservoir for example or a container. Preferably, however, the at least one source is a syringe. The syringe may then be connected to the at least one needle channel. Preferably, an actuator is foreseen to separately actuate the syringe when the medicinal solution is to be injected. Advantageously, a relationship between the actuating force acting on the syringe and the volume of solution injected is then implemented in the microcontroller.

Usually, the robotic system also comprises a workstation including a computer, navigational display, and haptic control mechanism for remote control (joystick or touch screen) allowing a physician to interact with the autonomous software and user interface through the microcontroller if necessary.

A preferred embodiment of the robotic system comprises a robotic arm and an outer robotic handle. Both, the robotic arm and the outer robotic handle may be formed by constructing 3D printed structures made up of 70% polylactic acid (PLA) infill. Industrial grade cyanoacrylate adhesive or nuts and bolts may be used to fix appropriate components together and ball bearings may be used to slide the robotic arm within the outer robotic handle. Stepper motors may be used as actuators for four pull wires, a needle and the robotic arm. The stepper motors may be assembled onto 10 cm linear mechanical slides. Both, the pull wires and the robotic arm may be attached to 3D printed connectors, which in turn, are fastened onto their respective mechanical slide. The actuators for the pull wires may be attached to the robotic arm while the actuator for the robotic arm may be fixed onto the outer robotic handle. A needle channel may be connected to a syringe that is locked into a mobile contraption within the robotic arm. The linear movement of this contraption, and thus the needle, may be controlled by a stepper motor attached to the robotic arm. In this manner, the actuation of the pull wires and the needle within the inner operating catheter is independent of the actuation of the robotic arm. If the robotic arm, and thus the inner operating catheter, is actuated, the pull wires, the needle, and their actuators and slides maintain their relative position within the inner operating catheter body as they are fixed onto the robotic arm.

The present invention is moreover directed to a process for operating a robotic system comprising an autonomously controllable pull wire injection catheter according to the invention, a robotic arm, a microcontroller, a holder and contraption for at least one source of medicinal solution, wherein the robotic arm is manoeuvrable at least in forward and backward direction, wherein the inner operating catheter of the autonomously controllable pull wire injection catheter is fixed onto the robotic arm as such that the catheter handle, the at least one needle, the at least one contact force sensor, the at least one electrode, and each of the at least four actuator driven pull wires are separately connected to the robotic arm, and wherein the robotic arm is adapted to be controlled by the microcontroller, wherein the process comprises the following steps:

(a) Position the autonomously controllable pull wire injection catheter in an operating environment so as to situate the tip of the inner operating catheter on a desired surface;

(b) Calibrate the at least one electrode and the tip of the inner operating catheter with respect to its movement and orientation;

(c) Manipulate the tip of the inner operating catheter so as to sample the surface area for one or more injection sites according to a measured electrical potential difference and actuate the at least one needle and the at least one syringe to inject the at least one medicinal solution at the determined injection site;

(d) Repeat step (c) until the desired surface area is sampled and return the tip of the inner operating catheter to its position in step (a).

According to the inventive process in step (a) the autonomously controllable pull wire injection catheter is positioned in an operating environment so as to situate the tip of the inner operating catheter on a desired surface.

In a preferred embodiment the operating environment is the heart of a patient and the surface is the endocardium wall of the left ventricle. The outer catheter guide is then positioned in the aorta one fourth of the way into the left ventricle applying e.g. the standard protocol of incision via the femoral artery. A guide wire may be first inserted through the incision and passed through the femoral artery towards the descending aorta. The outer guide can then be passed over the guide wire and slid through the descending and ascending aorta through the aortic valve. Once the guide is in place, the outer handle is fixed in place and rendered immobile e.g. on a stabilizing arm. The inner operating catheter is then passed through the the outer catheter guide until it reaches the position in the interior of the left ventricle. The inner operating catheter tip is then placed upon the apex of the left ventricle.

According to the inventive process in step (b) the at least one electrode and the tip of the inner operating catheter with respect to its movement and orientation are calibrated.

The first calibration is to determine the electrical potential of a healthy surface in a patient's body, i.e. healthy myocardium as a reference by activating the electrode. Knowing the electrical potential of the healthy surface then allows the system to determine when it comes into contact with sites of different electrical potential. In the case of infarct boundaries these may be site of lower potential or electrical silence for example.

The second calibration is to determine the relationship between the inner operating catheter tip and the movement the actuators controlling the respective pull wires. Calibration of the tip's movement in comparison to the movement of the actuators can be realized in a feedback and/or feedforward manner by adjusting existing empirical models or compensation functions in an operational software due to discrepancies caused by friction, backlash, or the tension and compression forces. The inner operating catheter may be moved back and forth and deflected while the position of the tip is recorded by either an image analysis or a location sensor for example. The tip position can then be compared to the projected position pre-integrated in software installed on the microcontroller. If any discrepancies are apparent, the parameters for the existing mathematical functions in the software can be adjusted accordingly.

The third calibration is to verify the orientation of the inner operating catheter tip with respect to the anatomical structure of the surface, e.g. an individual left ventricle. In the case of a beating heart, software for sampling an area on a left ventricle may be adjusted to the orientation of the inner operating catheter tip within the left ventricle for example. The system may then also be calibrated in both systole and diastole to ensure that the inner operating catheter tip stays in contact with the myocardial wall irrespective of systole and diastole. Furthermore, an image analysis algorithm may also be used to determine the location of the tip by identifying certain structures within a left ventricle. The catheter tip may then be autonomously deflected at a preordained orientation until it comes into contact with the endocardium. The software can then proceed to match the tip location to the appropriate segment of the left ventricle. This calibration may also be performed several times in systole and diastole.

The above calibration procedures are not limiting and may be performed in an analogous way for different operational environments.

In a preferred embodiment the microcontroller may be pre-programmed to sample a certain surface area in a patient's body.

Advantageously, the inner operating catheter tip has sufficient contact to the surface while sampling the surface area in step (c). In a preferred embodiment a feedback signal from the at least one force sensor may indicate sufficient contact with a surface in a patient while sampling the surface area.

If the surface is for example the endocardium wall of a left ventricle, manipulation of the inner operating catheter tip to stay situated on the endocardium surface may advantageously be accomplished by actuating the respective pull wires and deflecting the tip in accordance with a signal received by the contact force sensor. If the sensor reads that no contact is established or if the contact force is too high, the tip of the catheter can then autonomously be shifted towards or away from the contact point by the microcontroller.

In the case of a beating heart for example, an increasing contact force would indicate that the left ventricle is contracting and a decreasing contact force would indicate that the left ventricle is expanding. To ensure that the tip of the inner operating catheter continuously maintains contact with a certain spot on a moving location such as the left ventricle of a beating heart for example, the following approaches may be feasible. If the inner operating catheter can be elastically deformed its distal end may bend in harmony with the beating left ventricle. Another approach may be to use an image analysis algorithm to provide feedback on the movement of the left ventricle structures and on the catheter. An additional approach may be to adjust the catheter angle as such that its advancement is orthogonal with respect to the wall of the left ventricle.

During sampling a surface area within a patient, a measured electrical potential may indicate an injection site.

An infarct area for example typically has little or no electrical potential as the scarred tissue is less conductive than the surrounding myocardial muscle. For instance, scar tissue can have a bipolar reading of less than 0.5 mV while viable myocardium would read at 1.5 mV or higher. At the infarct boundary, the voltage reading would lie in between this range. Therefore, a clear reading in between these two values can indicate the presence of an infarct boundary. The microcontroller may then relocate the catheter tip accordingly to a location in between these two coordinates where the infarct boundary is present and hence an injection site. The microcontroller may then automatically insert the needle and inject a medicinal solution by activating the respective actuators. Then it may move onto the next location.

In an embodiment injection occurs during the left ventricle's expansion as the interstitial space between cells becomes more compact during contraction, thus increasing the pressure at the needle and cell interface.

In a preferred embodiment the needle may be actuated by the microcontroller as such that an injection can be performed diagonally with respect to the surface. In the case of an infarct boundary for example, dispersing the cell solution as much as possible in the infarct boundary area can be achieved, which leads to an ideal situation for which the cells can differentiate along the myocardial tissue and proliferate into the infarct area. Diagonal dispersion may be advantageously accomplished by using a pre-shaped, curved needle and injecting the solution as the needle is being retracted.

Advantageously, after every injection, the catheter tip may be slightly retracted and moved away from the surface so that the catheter tip may be readjusted to approach the next site orthogonally. If two injection sites are too close to each other, the microcontroller may induce injection only once.

In a preferred embodiment of the inventive process, a total volume of from 5-15 mL of solution is injected in step (c). For example 10 mL are injected. In a moreover preferred embodiment the total number of injections in step (c) is of from 10 to 25. Particularly preferred is a total number of 20 injections in the case of injections into the left ventricle of a beating heart as increasing the total number of injections above 20 may cause cardiac infarction.

According to the inventive process, in step (d) step (c) is repeated until the desired surface area is sampled and the tip of the inner operating catheter is returned to its position in step (a).

The designated surface area of where the system should sample for injection sites may be predefined in a software algorithm. For the left ventricle, it is important to note, that it is essential to avoid the chordae tendineae, its point of connection to the papillary muscles, and the aortic and mitral valve in the basal region of the left ventricle. Avoidance of these areas can be accomplished by identifying these structures through image recognition and analysis software. The system then avoids these areas based on those images.

For the left ventricle, predefinition in the software algorithm can be performed based on the 17 segment model recommended by the American Heart Association (AHA), the catheter then consequently searches in the apical region (segments 13-16; the apical anterior, apical septal, apical inferior, apical lateral respectively) and a portion of the mid-cavity region (segments 8, 9 and partially 7, 10; the mid anteroseptal, mid inferoseptal, mid anterior, mid inferior, respectively).

Another method would be to have for example a physician enter into a user interface the segments of the left ventricle where infarcts are known to be located. In this manner, the catheter can directly search in the general area of the infarct instead of moving to every designated point in the left ventricle.

The inventive process allows varying levels of autonomy with one or more steps being carried out by a physician. In a preferred embodiment, however, steps (b) to (d) are performed completely autonomous by the microcontroller.

The robotic system of the present invention can be controlled using any control system or model (including, but not limited to PID control, PID control with inverse kinematics, machine learning techniques, fuzzy logic controller, lumped parameter models).

Moreover, the robotic system of the present invention is adaptable to other diagnostic and therapeutic catheters, not just to catheters for injections.

The autonomously controllable pull wire injection catheter and the robotic system comprising an autonomously controllable pull wire injection catheter of the present invention are described above especially with regard to the treatment of cardiovascular diseases. It is however also possible to use this catheter and the robotic system to treat cancer by implanting myoblasts into tumors. The implantation of myoblasts in tumors is described in EP 2 837 683 A1 and in LAW. P. K. et al., World's First Myoblast Treatment of Human Cancer Found Safe and Efficacious", OPEN JOURNAL OF REGENERATIVE MEDICINE, 31 Mar. 2017, vol. 6, pages 1 to 16.

In this regard, the autonomously controllable pull wire injection catheter and the robotic system comprising an autonomously controllable pull wire injection catheter of the present invention can be advantageously used. The autonomous robotic catheter control system may use electric, force, pressure, ultrasound, and/or electromagnetic sensor(s) for accurate detection of solid tumors.

The invention has numerous advantages. As the mechanisms controlling the pull wire injection catheter are actuators that, in turn, are controlled by a microcontroller and not a human, the injection process can be carried out completely autonomously without the interaction of a physician. The inventive robotic system is able to completely autonomously: 1) self-calibrate the catheter position, 2) move the catheter around to search for injection sites, 3) stabilize itself on moving surfaces by means of actuators that can react to the feedback from force sensors, 4) detect damaged or degenerated sites, 5) insert a needle, and 6) inject medicinal solution, preferably at a diagonal angle while retracting the needle. None of these tasks are to be accomplished by remote control or with human involvement, meaning that a physician only needs to insert the catheter, wait for the system to perform the operation, and then retract the catheter. In this way, the physician to conduct the operation may just observe the procedure from a distant work station, safe from possible radiation exposure, if the procedure involves imaging techniques.

The invention will be described below by referring to FIGS. 1 to 4. The Figures show embodiments of the present invention. Other embodiments are conceivable.

Figure 1:
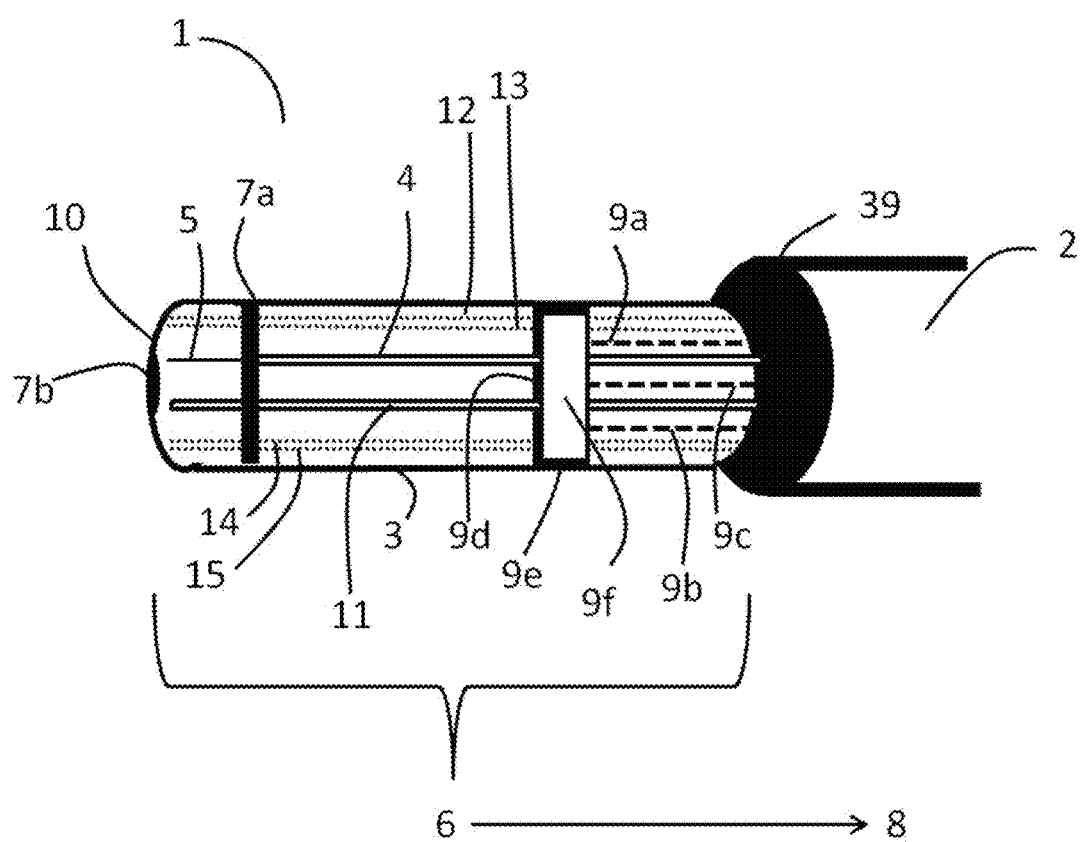
FIG. 1 shows a schematic of an autonomously controllable pull wire injection catheter according to an embodiment of the invention.

FIG. 1 depicts a schematic representation of an autonomously controllable pull wire injection catheter 1 according to an embodiment of the invention. The catheter 1 comprises an outer catheter guide 2 and an inner operating catheter 3, wherein the inner diameter of the outer catheter guide casing 39 is large enough to pass the inner operating catheter 3 through the outer catheter guide 2. The inner operating catheter 3 further comprises a needle channel 4 having a nickel titanium alloy needle 5 of 0.5 mm (25 gauge) in the distal region 6. The inner operating catheter 3 comprises a reference ring electrode 7a, 7b in the distal region 6, wherein the sensor 7b is disposed at the tip 10 of the inner operating catheter 3 and the reference ring 7a in the vicinity of the tip 10. The electrode 7a, 7b has a connection running along the inner operating catheter 3 to the proximal region 8 so as to be activated by a proximal connection, i.e. to a microcontroller (not shown). An optical fiber contact force sensor 9a-f is moreover arranged at the distal end 6 of the inner operating catheter 3. The contact force sensor 9a-f is a fiber optic sensor comprising three single mode fibers 9a-c, a reflective surface 9d, an air gap 9f and an elastic material 9e. If light is passed through one of the optical fibers it is reflected by the reflective surface 9d. If the tip 10 of the inner operating catheter 3 is subjected to a contact force, the elastic material 9e will be compressed reducing the air gap 9f. The reduction of the air gap 9f in turn leads to a deviation in the light signal reflected by the surface 9d, which can be correlated to the contact force acting on the tip 10 of the inner operating catheter 3. In this, the contact force sensor 9a-f can detect a contact force between the tip 10 of the inner operating catheter 3 and/or the needle 5, if it is protruded from the tip 10, and a surface that is touched by the inner operating catheter 3. An anticoagulant channel 11 is provided in the inner operating catheter 3 through which an anticoagulant can be pumped if necessary. The tip 10 of the inner operating catheter 3 can be manipulated by a set of 4 actuator driven (not shown) kevlar pull wires 12, 13, 14, 15 attached perpendicular to each other at a pre-defined distance from the tip 10 in the distal region 6.

Figure 2:
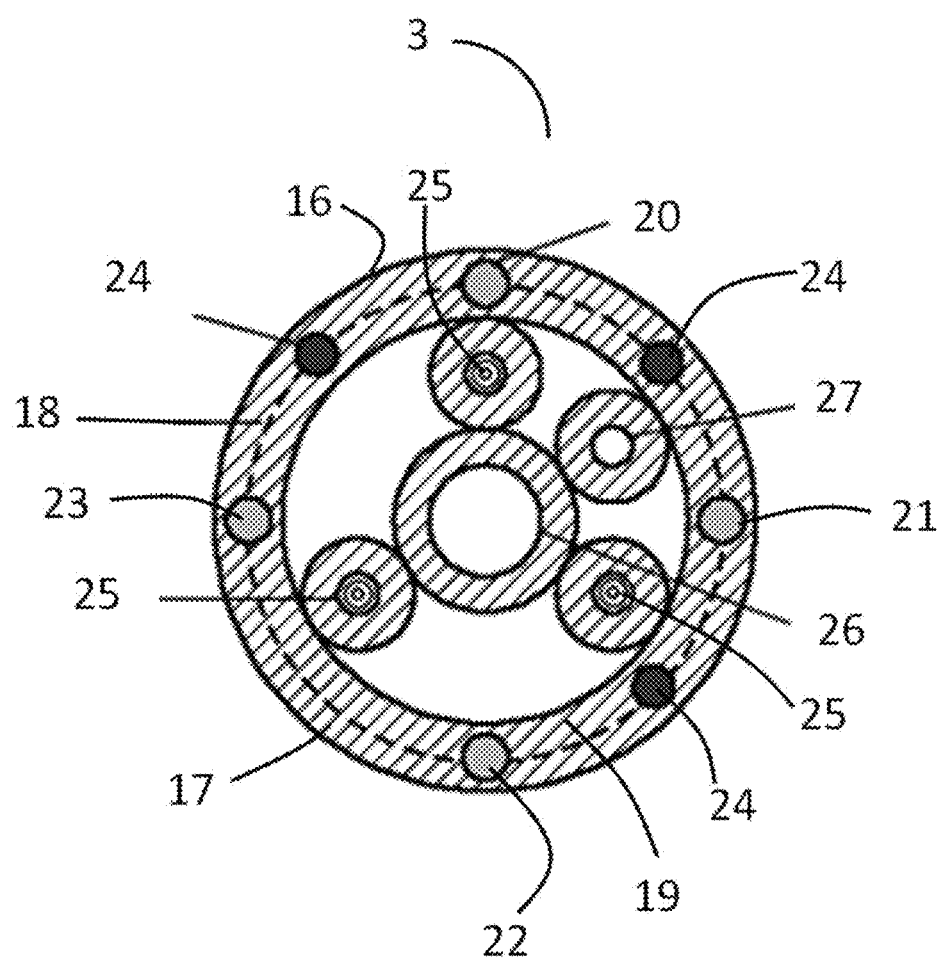
FIG. 2 shows a schematic cross section of an inner operating catheter as used in an embodiment of the autonomously controllable pull wire injection catheter according to the invention.

FIG. 2 depicts a cross section of an inner operating catheter 3 as used in an embodiment of the autonomously controllable pull wire injection catheter 1 according to the invention. The inner operating catheter casing 16 has a circular cross section with an outer diameter of 2.7 mm. The wall of the inner operating catheter casing 16 consists of an outer layer of thermoplastic polyurethane (TPU) 17, a braided or coiled stainless steel middle layer 18, and an inner layer of polytetrafluoroethylene (PTFE) 19. Within the wall of the catheter casing 16, four actuator driven (not shown) stainless steel pull wires 20, 21, 22, 23 and lead wires for electrodes 24 are embedded and can thus be passed from the proximal to the distal region of the catheter 3. Three optical fibers 25 of 0.25 mm in diameter are shown, creating an optical fibre contact force sensor at the tip of the inner operating catheter 3 in combination with an elastic material and a reflective surface provided thereon (not shown). A needle channel 26 and an anticoagulant channel 27 adapted to provide the anticoagulant heparin also extend from the distal to the proximal region of the inner operating catheter 3.

Figure 3:
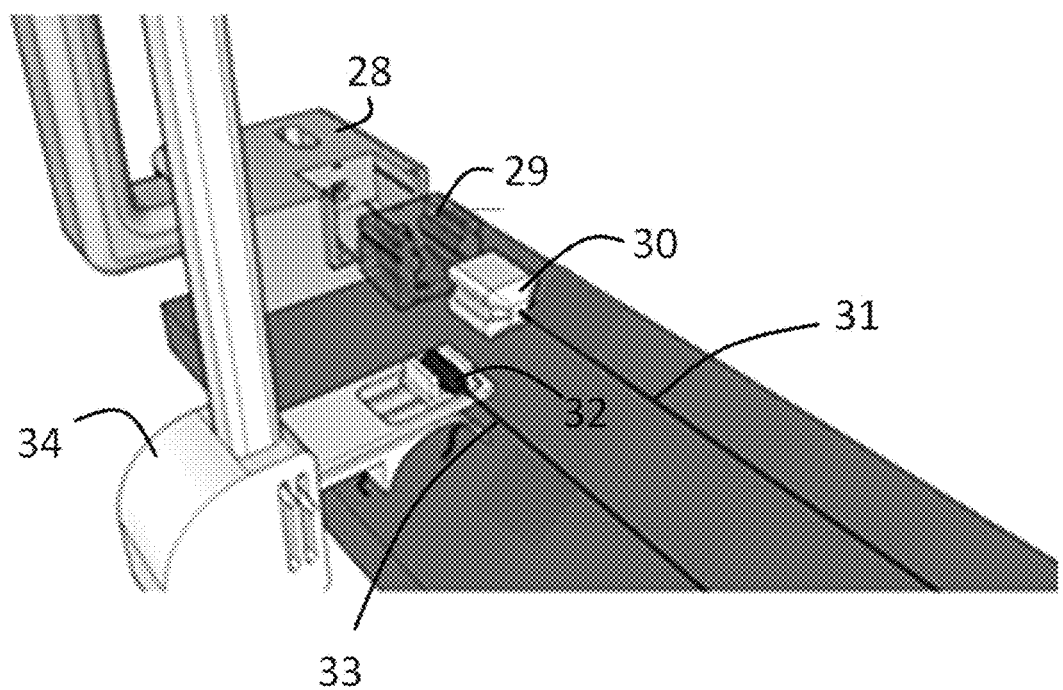
FIG. 3 shows a schematic of parts of a robotic system according to an embodiment of the invention.

FIG. 3 depicts a schematic of parts of a robotic system according to the invention. A part of a robotic arm 28 is shown that can be locked to a patient's bed rail (not shown). The handle 30 of the inner operating catheter 31 can be fixed to the robotic arm 28 via a disposable connector 29. In this embodiment the robotic system further comprises a stabilizing arm 34 to hold the outer catheter guide 33 in place by locking the outer catheter guide handle 32 after it has reached its desired position in the body of a patient.

Figure 4:
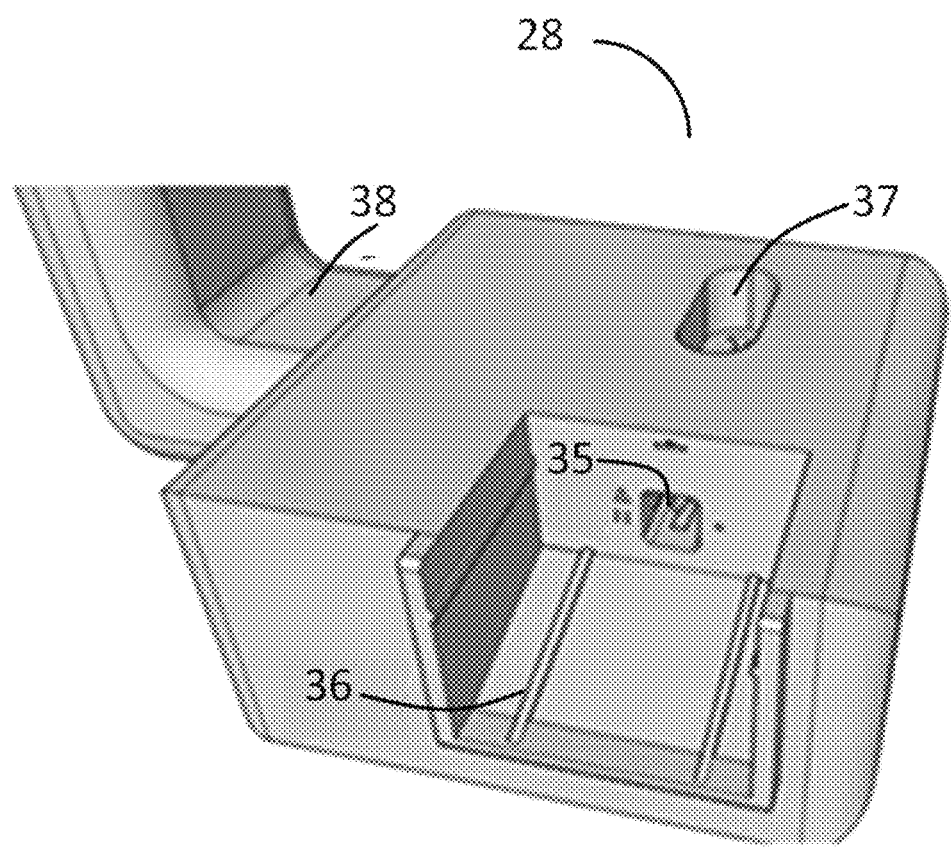
FIG. 4 shows a schematic of details of a robotic arm as used in an embodiment of the robotic system according to the invention.

FIG. 4 depicts a schematic of details of a robotic arm 28 as used in an embodiment of the robotic system according to the invention. The robotic arm 28 comprises female connectors 35 for at least one electrode, optical fibers of a force sensor, at least four actuator driven pull wires, at least one needle channel and a heparin channel. The robotic arm 28 further comprises a mobile platform 36 to which an inner operating catheter 3, 31 as used in embodiments of the autonomously controllable pull wire injection catheter 1 according to the invention can be fixed. The mobile platform 36 may be moved back and forth by an actuator (not shown). The robotic arm 28 comprises moreover a holder and a contraption for a syringe 37. In this embodiment the head 38 of the robotic arm 28 is rotatable.

REFERENCE NUMERALS 1 autonomously controllable pull wire injection catheter
2 outer catheter guide
3 inner operating catheter
4 needle channel
5 needle
6 distal region
7a electrode (reference ring)
7b electrode (sensor)
8 proximal region
9 fiber optic contact force sensor
9a-c optical fibers
9d reflective surface
9e elastic material
9f air gap
10 tip of the inner operating catheter
11 anticoagulant channel
12 actuator driven pull wire, kevlar
13 actuator driven pull wire, kevlar
14 actuator driven pull wire, kevlar
15 actuator driven pull wire, kevlar
16 inner operating catheter casing
17 outer layer, thermoplastic polyurethane
18 middle layer, stainless steel, braided or coiled
19 inner layer, polytetrafluoroethylene
20 actuator driven pull wire, stainless steel
21 actuator driven pull wire, stainless steel
22 actuator driven pull wire, stainless steel
23 actuator driven pull wire, stainless steel
24 electrode lead wire
25 optical fiber, contact force sensor
26 needle channel
27 anticoagulant channel, heparin channel
28 robotic arm (part of)
29 disposable connector
30 inner operating catheter handle
31 inner operating catheter
32 outer catheter guide handle
33 outer catheter guide
34 stabilizing arm
35 female connectors
36 mobile platform
37 holder and contraption for a syringe
38 rotatable head of the robotic arm
39 outer catheter guide casing

The invention claimed is:

1. Autonomously controllable pull wire injection catheter (1) comprising an outer catheter guide (2, 33) having an outer catheter guide casing (39) and an inner operating catheter (3, 31) having an inner operating catheter casing (16), wherein the inner operating catheter (3, 31) comprises a catheter handle (30), a catheter tip (10), at least one needle (5) that is connected to at least one source of medicinal solution via at least one needle channel (4, 26), at least one contact force sensor (9a-f, 25), at least one electrode (7, 24), at least four actuator driven pull wires (12-15, 20-23) for moving the tip (10) of the inner operating catheter (3, 31), wherein the inner diameter of the outer catheter guide casing (39) is larger than the outer diameter of the inner operating catheter casing (16), characterized in that the inner operating catheter (3, 31) is adapted to be controlled by a microcontroller, wherein the at least one electrode (7, 24) and the at least one contact force sensor (9a-f, 25) are adapted for data exchange with the microcontroller, and wherein the at least four actuator driven pull wires (12-15, 20-23) are attached inside the inner operating catheter (3, 31) perpendicular to each other at a pre-defined distance from the tip (10) in the distal region (6).

2. Catheter (1) according to claim 1, characterized in that the autonomously controllable pull wire cell injection catheter (1) further comprises an electromagnetic position sensor.

3. Catheter (1) according to claim 1, characterized in that the at least one electrode (7, 24) is adapted to operate in Laplacian mode.

4. Catheter (1) according to claim 1, characterized in that the inner operating catheter (3, 31) comprises eight actuator driven pull wires.

5. Catheter (1) according to claim 1, characterized in that the casing (16) of the inner operating catheter (3, 31) has a wall that consists of at least three layers with an outer layer (17) of thermoplastic polyurethane, a braided or coiled stainless steel middle layer (18), and an inner layer (19) of perfluoroethylene (PTFE).

6. Catheter (1) according to claim 1, characterized in that the at least one contact force sensor (9a-f, 25) is a fiber optic sensor (9a-f).

7. Catheter (1) according to claim 1, characterized in that the at least one medicinal solution is a cell solution.

8. A robotic system comprising an autonomously controllable pull wire injection catheter (1) according to claim 1, a robotic arm (28), a microcontroller, a holder and contraption for at least one source of medicinal solution (37), characterized in that the robotic arm (28) is maneuverable at least in forward and backward direction, wherein the inner operating catheter (3, 31) of the autonomously controllable pull wire injection catheter (1) is fixed onto the robotic arm (28) as such that the catheter handle (30), the at least one needle (5), the at least one contact force sensor (9*a-f*, 25), the at least one electrode (7, 24), and each of the at least four actuator driven pull wires (12-15, 20-23) are separately connected to the robotic arm (28), and wherein the robotic arm (28) is adapted to be controlled by the microcontroller.

9. System according to claim 8, characterized in that the robotic system further comprises an imaging unit selected from the group consisting of an ultrasound unit, a magnetic resonance unit or a fluoroscopy unit.

10. System according to claim 9, characterized in that the imaging unit is a 3D or 4D ultrasound unit.

11. System according to claim 9, characterized in that the robotic arm (28) is made up of at least 70% of polylactid acid.

12. Process for operating a robotic system comprising an autonomously controllable pull wire injection catheter (1) according to claim 1, a robotic arm (28), a microcontroller, a holder and contraption for at least one source of medicinal solution (37), wherein the robotic arm (28) is maneuverable at least in forward and backward direction, wherein the inner operating catheter (3, 31) of the autonomously controllable pull wire injection catheter (1) is fixed onto the robotic arm (28) as such that the catheter handle (30), the at least one needle (5), the at least one contact force sensor (9*a-f*, 25), the at least one electrode (7, 24), and each of the at least four actuator driven pull wires (12-15, 20-23) are separately connected to the robotic arm (28), and wherein the robotic arm (28) is adapted to be controlled by the microcontroller, characterized in that the process comprises the following steps:

(a) Position the autonomously controllable pull wire injection catheter (1) in an operating environment so as to situate the tip of the inner operating catheter (3, 31) on a desired surface;

(b) Calibrate the at least one electrode (7, 24) and the tip (10) of the inner operating catheter (3, 31) with respect to its movement and orientation;

(c) Manipulate the tip (10) of the inner operating catheter (3, 31) so as to sample the surface area for one or more injection sites according to a measured electrical potential difference and actuate the at least one needle (5) and the at least one syringe to inject the at least one medicinal solution at the determined injection site;

(d) Repeat step (c) until the desired surface area is sampled and return the tip (10) of the inner operating catheter (3) to its position in step (a).

13. Process according to claim 12, characterized in that a total volume of from 5-15 mL of solution is injected in step (c).

14. Process according to claim 12, characterized in that the total number of injections performed in step (c) is of from 10 to 25.

15. Process according to claim 12, characterized in that steps (b) to (d) are performed by the microcontroller.

* * * * *